(12) United States Patent
Beatson et al.

(10) Patent No.: US 6,760,161 B2
(45) Date of Patent: Jul. 6, 2004

(54) MULTI-COLOR MACHINE VISION SYSTEM

(75) Inventors: David T. Beatson, Kennett Square, PA (US); Christian Hoffman, Willow Grove, PA (US); Michael Woodward, Ardsley, PA (US); Lawrence B. Brown, Cochranville, PA (US)

(73) Assignee: Kulicke & Soffa Investments, Inc., Wilmington, DE (US)

( * ) Notice: Subject to any disclaimer, the term of this patent is extended or adjusted under 35 U.S.C. 154(b) by 0 days.

(21) Appl. No.: 10/336,458

(22) Filed: Jan. 3, 2003

(65) Prior Publication Data

US 2003/0099041 A1 May 29, 2003

Related U.S. Application Data

(63) Continuation of application No. 09/961,742, filed on Sep. 24, 2001, now Pat. No. 6,529,333.

(51) Int. Cl.⁷ .............................................. G02B 27/14
(52) U.S. Cl. ..................................... 359/634; 359/629
(58) Field of Search ................................. 359/629, 634, 359/636, 638, 354, 355, 618, 583, 589, 722, 723; 250/208.1, 223 R, 221, 216; 353/31–34, 37, 38, 40

(56) References Cited

U.S. PATENT DOCUMENTS

| | | | | |
|---|---|---|---|---|
| 3,985,854 A | * | 10/1976 | Bradford et al. | ............... 423/22 |
| 5,048,926 A | | 9/1991 | Tanimoto | |
| 5,515,169 A | * | 5/1996 | Cargill et al. | ............... 356/417 |
| 5,751,473 A | * | 5/1998 | Runciman | .................. 359/355 |
| 5,982,493 A | | 11/1999 | Lehnen et al. | |
| 6,008,943 A | | 12/1999 | Metelitsa | |
| 6,407,867 B1 | | 6/2002 | Hildebrandt | |

* cited by examiner

Primary Examiner—Georgia Epps
Assistant Examiner—Alicia M. Harrington
(74) Attorney, Agent, or Firm—RatnerPrestia

(57) ABSTRACT

A method and system for providing different magnified images of an electronic device. The vision system has a first beamsplitter for receiving an image of the device illuminated by a light source, the beamsplitter providing multiple images of the device; optical elements for receiving the plural images of the device, each of the optical elements magnifying the image by a predetermined magnification factor to produce more than one magnified images; and a second beamsplitter for receiving the magnified images and filtering out all but one of the magnified images based on a wavelength of the light source.

15 Claims, 6 Drawing Sheets

MULTI-COLOR MACHINE VISION SYSTEM

This application is a continuation of U.S. patent application Ser. No. 09/961,742 filed Sep. 24, 2001, now U.S. Pat. No. 6,529,333.

FIELD OF THE INVENTION

This invention relates generally to machine vision systems for semiconductor chip bonding/attaching devices. More specifically, the present invention relates to an apparatus for providing different magnifications of an object based on the illumination color of the object.

BACKGROUND OF THE INVENTION

Semiconductor devices, such as integrated circuit chips, are electrically connected to leads on a lead frame by a process known as wire bonding. The wire bonding operation involves placing and connecting a wire to electrically connect a pad residing on a die (semiconductor chip) to a lead in a lead frame. Once all the pads and leads on the chip and lead frame have been wire bonded, it can be packaged, often in ceramic or plastic, to form an integrated circuit device. In a typical application, a die or chip may have hundreds or thousands of pads and leads that need to be connected.

There are many types of wire bonding equipment. Some use thermal bonding, some use ultra-sonic bonding and some use a combination of both. Prior to bonding, vision systems or image processing systems (systems that capture images, digitize them and use a computer to perform image analysis) are used on wire bonding machines to align devices and guide the machine for correct bonding placement.

Machine vision systems are generally used to inspect the device before, during or after various steps in the fabrication process. During such process steps, it may be necessary to obtain multiple views of the device under different magnification levels to determine whether the device meets predetermined quality standards. One measurement may require a large field of view to include as many fiducals as possible, while a second measurement may require a high resolution to image fine details.

In conventional systems, such multiple magnifications are handled by having a separate camera for each desired magnification level. Such a conventional device is shown in FIG. 1. In FIG. 1, imaging device 100 includes objective lens 104, aperture 106, beam splitter 108, mirror 110, relay lenses 112, 114, and cameras 116, 118. In operation an image of device 102 is transmitted through object lens 104 as transmitted image 120 and in turn through aperture 106 as image 122. Image 122 is incident on beam splitter 108, which in turn divides the light from image 122 into first divided light rays 124 and second divided light rays 126. Divided light rays 126 are then redirected by mirror 110 as divided light 128.

Relay lenses 112 and 114 are selected so as to provide the desired magnification of divided light 124 and 128, respectively, resulting in magnified images 130 and 132, which are incident on cameras 116 and 118, respectively. This system has a drawback, however, in that it requires a separate camera for each level of magnification desired, thereby increasing size and cost.

A second conventional system is shown in FIGS. 2A and 2B. In FIGS. 2A and 2B, a shutter 218 is used in combination with a second beam splitter 222 to receive two magnifications of device 202 with a single camera 216. As shown in FIG. 2A, first beamsplitter 208 separates light rays 224 into light rays 226, 228, each being of about equal illumination, that is each of light rays 226, 226 is about half the illumination of light rays 224. When shutter 218 is in a first position, light rays 226 are prevented from reaching relay lens 214. On the other hand, light rays 228 are magnified by relay lens 212 to become magnified light rays 230. In turn, magnified light rays 230 are incident on second beamsplitter 222, a portion (about 50%) of which is transmitted to camera 216 as light rays 236. The remaining portion of magnified light rays 230, however, is deflected by second beamsplitter 222 as lost light rays 234. As a result, only about 25% of the light used to illuminate device 202 is actually received at camera 216. In addition, the inclusion of shutter 218 increases the complexity and cost of this system.

Alternatively, when shutter is in a second position, light rays 228 are prevented from reaching relay lens 212, while light rays 226 are directed through relay lens 214 by mirrors 210, 220 as magnified light rays 232. Similar to FIG. 2A, a portion 236 of magnified light rays 232 are received by camera 216 while remaining light rays 234 are lost. As is evident, a large portion of the illumination available for imaging is sacrificed due to the losses associated with first beam splitter 208 and second splitter 222. The light from a single channel hits the second splitter and is split into a reflected portion 234 and transmitted portion 236. Only one of these will be directed to camera 216 while the other is lost. This approach can also have reliability issues with respect to the moving shutter mechanism.

SUMMARY OF THE INVENTION

In view of the shortcomings of the prior art, it is an object of the present invention to provide one of multiple magnified views to an optical detector based on the wavelength of light illuminating the device being viewed.

The present invention is a vision system for use with a light source and providing a plurality of images of a device, the system comprises a first beamsplitter for receiving an image of the device illuminated by the light source, the beamsplitter providing a plurality of images of the device; a plurality of optical elements for receiving respective ones of the plural images of the device, each of the plurality of optical elements magnifying the image by a predetermined magnification factor to produce a plurality of magnified images; and a second beamsplitter for receiving the plurality of magnified images and filtering out all but one of the magnified images based on a wavelength of the light source.

According to another aspect of the invention, an optical detector receives the filtered magnified images from the second beamsplitter.

According to a further aspect of the invention, the optical detector is a camera.

According to still another aspect of the invention, the light has a wavelength in the visible spectrum.

According to yet another aspect of the present invention, the beamsplitters are dichroic splitters.

According to a further aspect of the invention, a first mirror is coupled between the first beam splitter and the second optical element and a second mirror is coupled between the second optical element and the second beam splitter.

These and other aspects of the invention are set forth below with reference to the drawings and the description of exemplary embodiments of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following Figures.

DETAILED DESCRIPTION

The entire disclosure of U.S. patent application Ser. No. 09/961,742 filed Sep. 24, 2001 is expressly Incorporated by reference herein.

Figure 1:
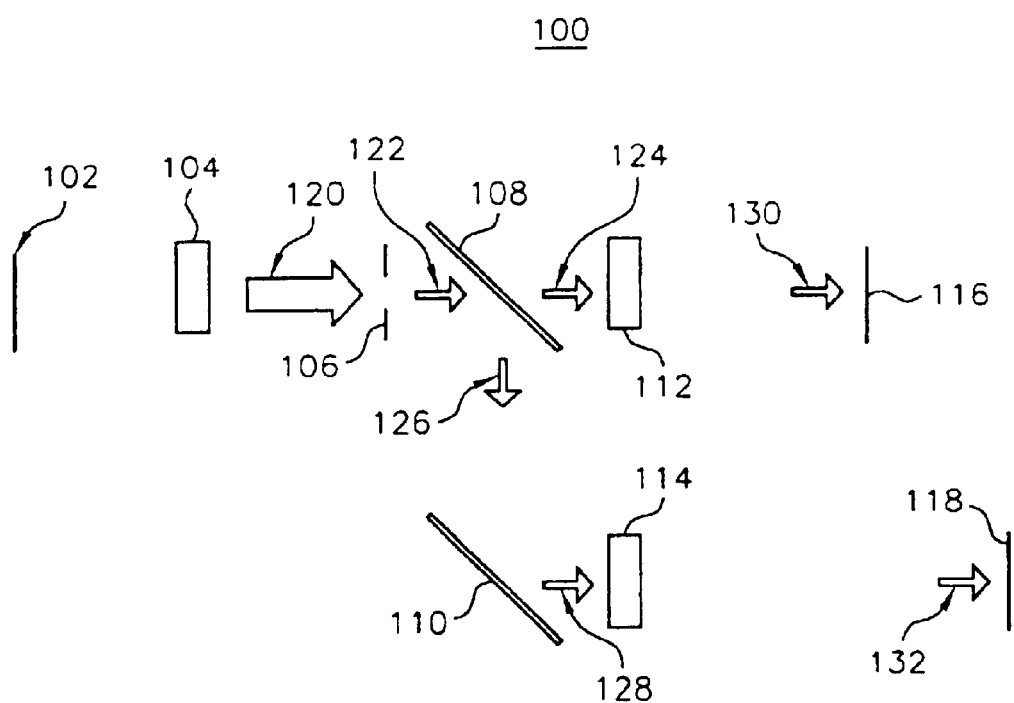
FIG. 1 is schematic representation of a vision system according to the prior art.
Figure 2A:
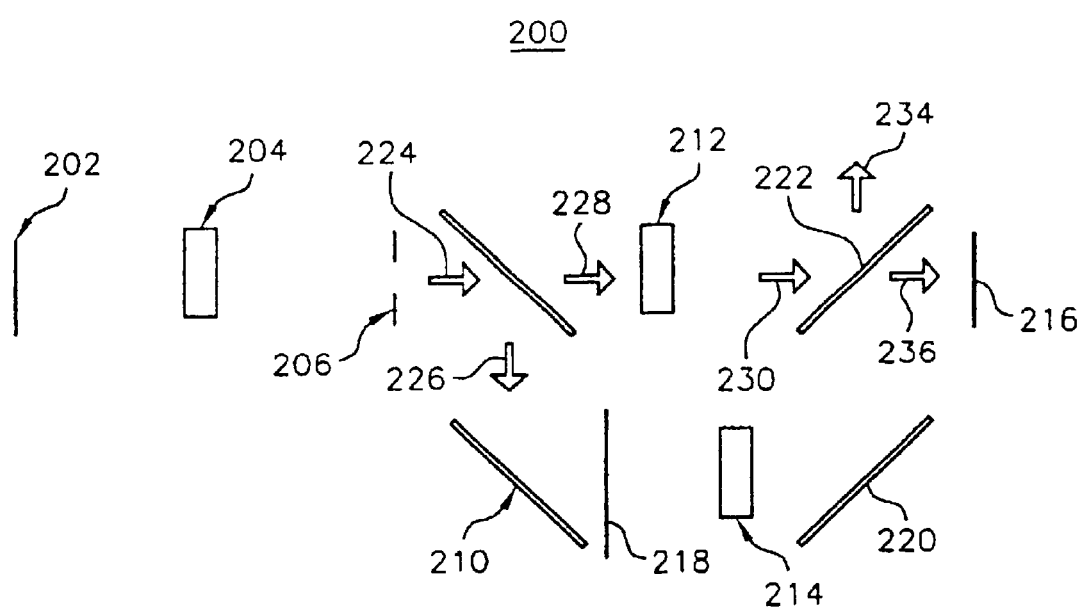
FIGS. 2A and 2B are schematic representations of another vision system according to the prior art.
Figure 2B:
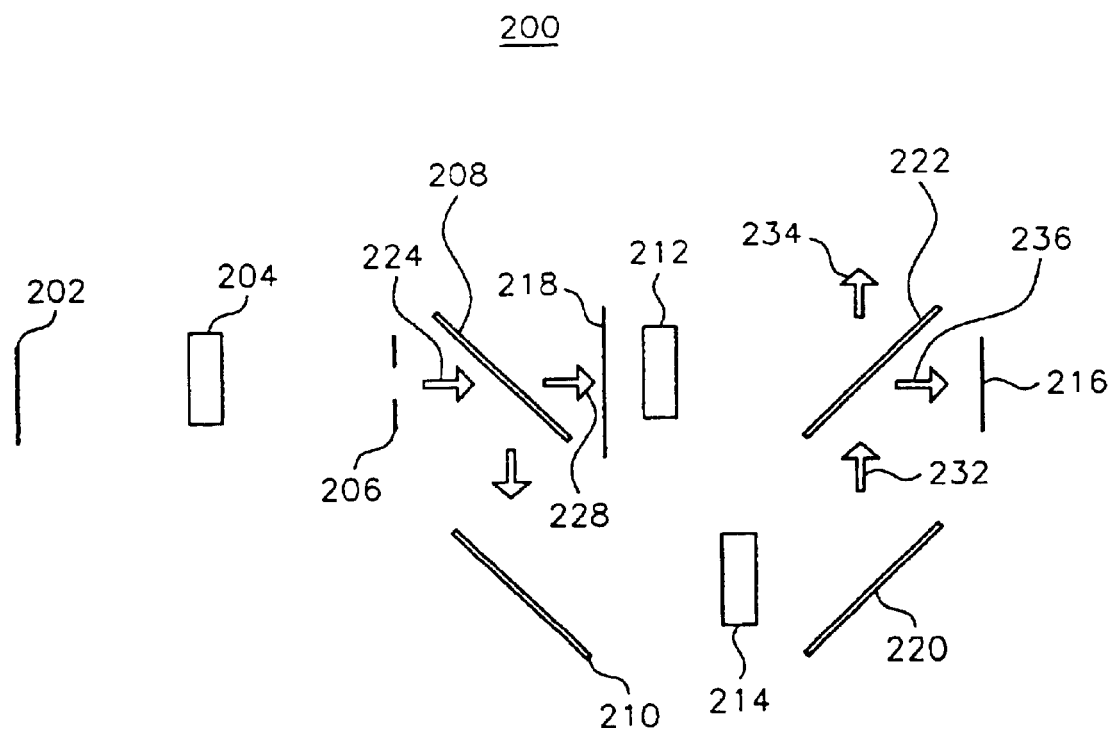
Figure 3A:
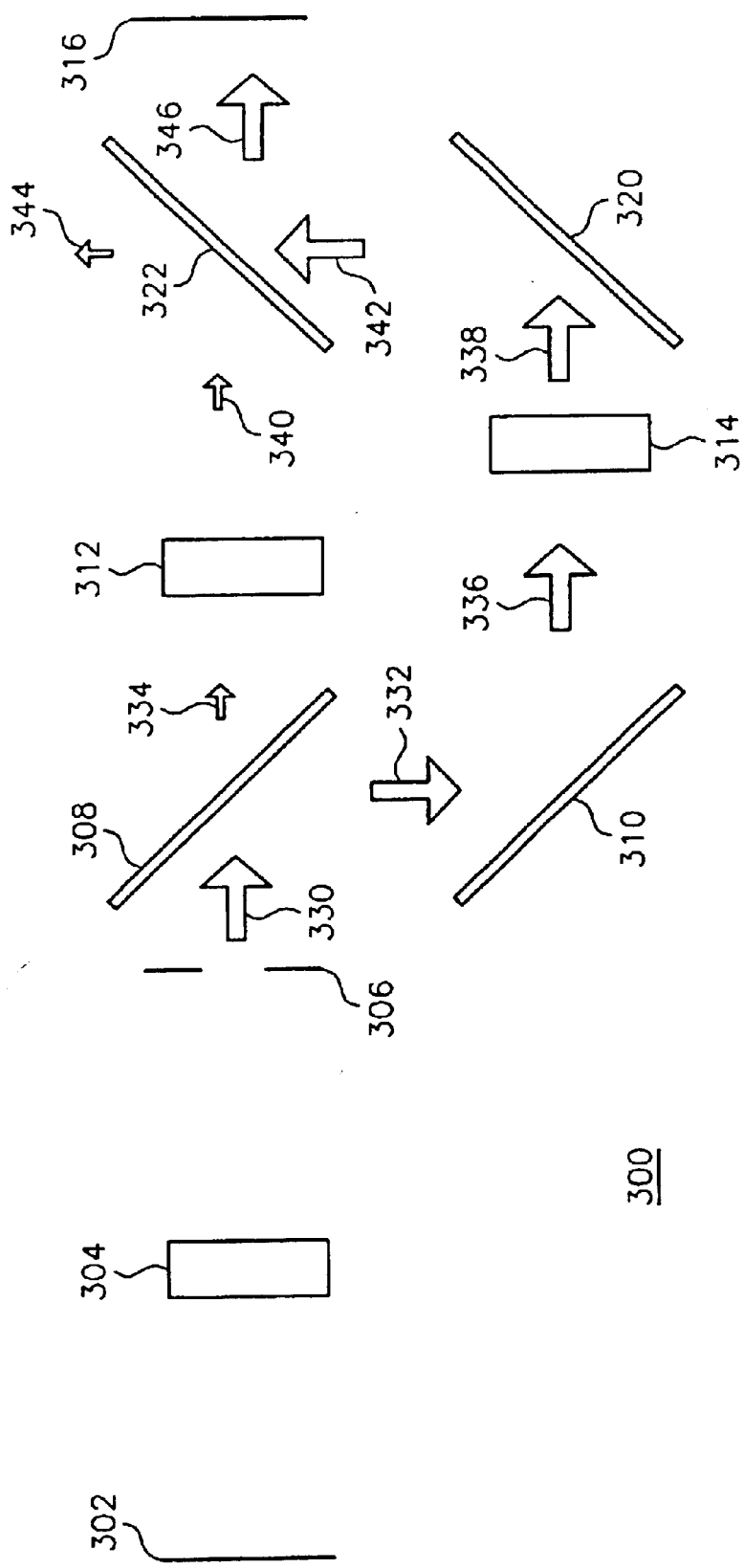
FIGS. 3A and 3B are schematic representations of a vision system according to a first exemplary embodiment of the present invention.
Figure 3B:
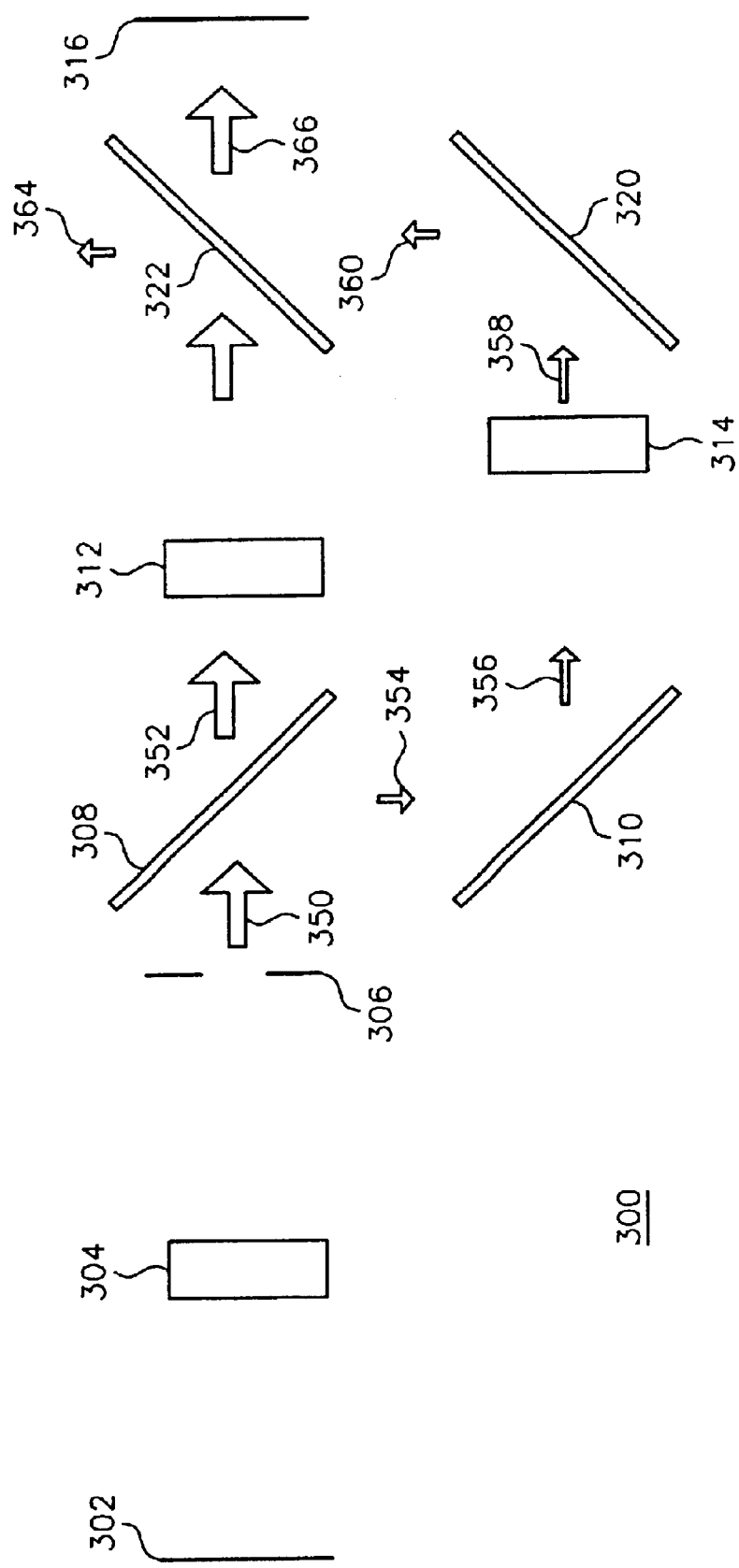

Referring to FIGS. 3A and 3B, an exemplary embodiment of the present invention is shown. In FIG. 3A, device 302 is illuminated by a light source (not shown) having a predetermined wavelength. In a preferred embodiment, this wavelength is within either the visible spectrum of light or ultraviolet spectrum of light. Light rays 330, representing an image of device 302, emerges from lens 304 and aperture 306. Light rays 330 are incident on dichroic splitter 308, which in turn reflects a substantial portion of light rays 330 as reflected light rays 332, based on properties of splitter 308 which are dependant upon the wavelength of light illuminating device 302. As dichroic splitters are not 100% efficient, a small portion of light rays 330 will pass through dichroic splitter 308 as light rays 334. Light rays 332 are then reflected by mirror 310, such as a planar mirror, as light rays 336 so as to allow them to be magnified by optical relay 314. In an exemplary embodiment, optical relay 314 is a doublet type lens assembly having a predetermined magnification factor. Based on this magnification factor, light rays 336 are magnified and emerge from optical relay 314 as magnified light rays 338. As is understood by those of skill in the art, magnified light rays 338 represent an enlarged image of device 302.

Magnified light rays 338 are again redirected by mirror 320 as magnified light rays 342 to be incident on a surface of dichroic splitter 322. In addition, light rays 334, having been magnified by a predetermined magnification factor by optical relay 312, are incident on an opposite surface of dichroic splitter 322 from that of magnified light rays 342. In an exemplary embodiment, the magnification factors of optical relays 312 and 314 are different from one another. Dichroic splitter 322 has properties, based on the wavelength of light illuminating device 302, such that the undesired image rays 340 do not pass through splitter 322, but rather are reflected away as discarded light 344. In this way multiple images are not provided to optical detector 316. On the other hand, dichroic splitter 322 has properties, based on the wavelength of light illuminating device 302, allowing magnified light rays 342 to be directed toward optical detector 316 as image rays 346. As a result, optical detector 316 "sees" only a single magnified image of device 302. In a preferred embodiment of the present invention optical detector 316 may be a camera, such as a CCD or CMOS camera, or a position sensitive detector (PSD).

Referring now to FIG. 3B, device 302 is illuminated by a light source (not shown) having a predetermined wavelength different for the wavelength of light that illuminated device 302 as described above with respect to FIG. 3A. In a preferred embodiment, this wavelength is within the visible spectrum of light. In FIG. 3B, light rays 350, representing another image of device 302, emerges from lens 304 and aperture 306. Light rays 350 are incident on dichroic splitter 308, which in turn passes a substantial portion of light rays 330 as light rays 352, based on properties of splitter 308 which depend upon the wavelength of light illuminating device 302. Once again, as dichroic splitters as not 100% efficient, a small portion of light rays 350 will be reflected by dichroic splitter 308 as reflected light rays 354. These light rays will in turn be redirected by mirror 310 as light rays 356, which will in turn be magnified by optical relay 314 as magnified light rays 358, which are then redirected toward dichroic splitter 322 by mirror 320 as reflected light 360.

Light rays 352 that emerge from dichroic splitter 308, pass through and are magnified by optical relay 312 to become magnified light rays 362. As a result, magnified light rays 362 are incident on dichroic splitter 322. As discussed above with respect to FIG. 3A, dichroic splitter 322 has properties, based on the wavelength of light illuminating device 302, such that undesired light rays 360 pass through splitter 322, and thus are directed away from optical detector 316 as discarded light 364. On the other hand, dichroic splitter 322 has properties, based on the wavelength of light illuminating device 302, allowing magnified light rays 362 to pass through splitter 322 as image rays 366. It is image rays 366 which are now "seen" by optical detector 316. In this way multiple images are not provided to optical detector 316 and different magnifications of device 302 may be provided merely by changing the wavelength of light that illuminates device 302.

Figure 4:
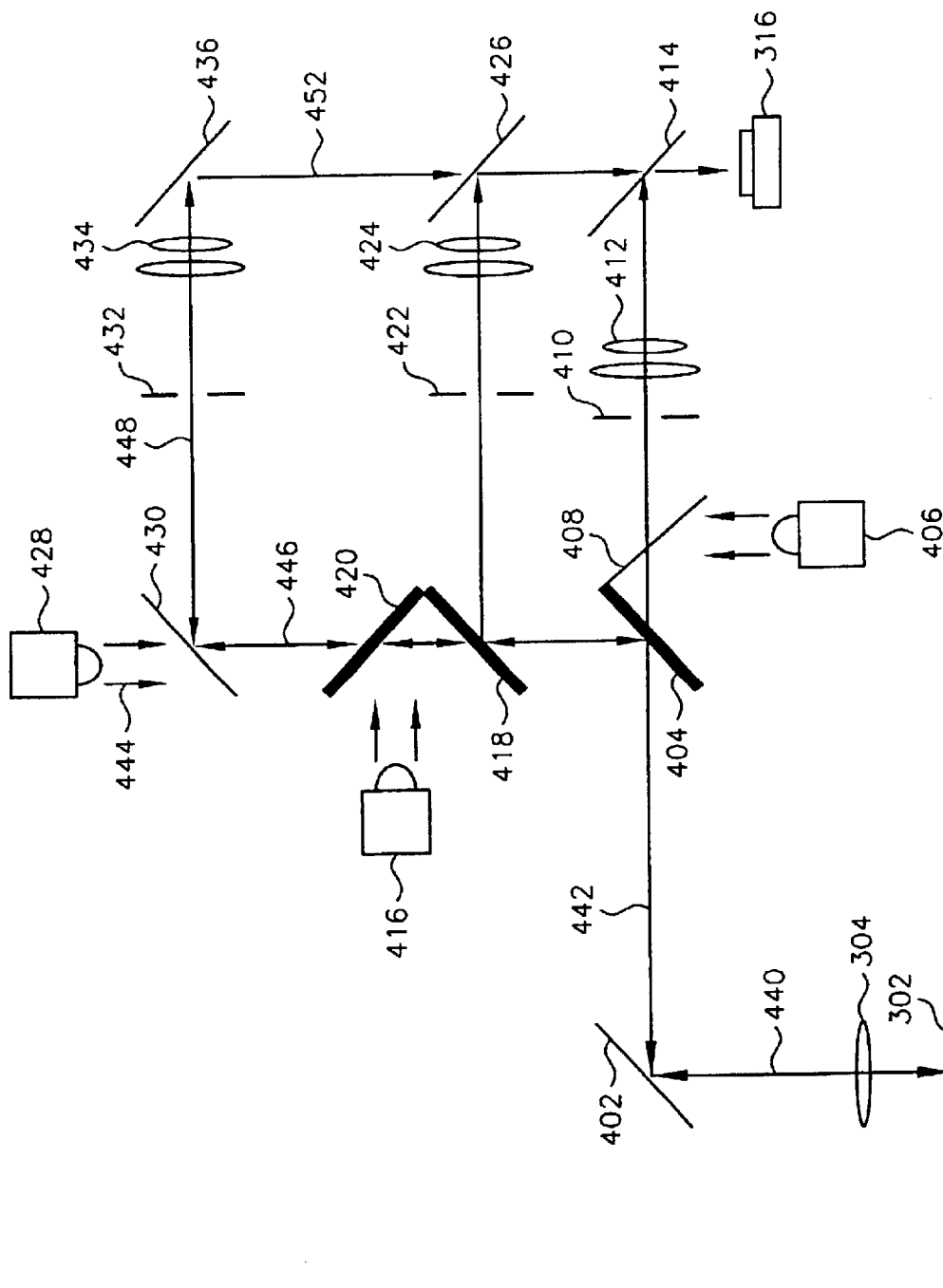
FIG. 4 is a schematic representation of a vision system according to a second exemplary embodiment of the present invention.

FIG. 4 illustrates a second exemplary embodiment of the present invention in which more that two light sources are used to illuminate device 302 and provide more that two different magnifications of device 302. In FIG. 4, device 302 is illuminated by one of light sources 406, 416, 428, each having a different wavelength. In a preferred embodiment, these wavelengths are within either the visible spectrum of light or ultraviolet spectrum of light. Illumination emitted by each of light sources is directed toward device 302 though a series of dichroic splitters 404, 418, 420, and 430. In the exemplary embodiment, only one light source is used to illuminate device 302 depending on the magnification desired. In the example illustrated in FIG. 4, light source 406 is used to provide magnification of device 302 through lens 412, light source 416 is used to provide magnification of device 302 through lens 424, and light source 428 is used to provide magnification of device 302 through lens 434. The magnification factor of each of lenses 412, 424, 434 is selected as desired. In a preferred embodiment of the present invention the magnification factor of lenses 412, 424, 434 is 2×, 6×, and 8×, respectively.

To illustrate how the second exemplary embodiment functions, a specific example is now discussed. If for example, it is desired to magnify an image of device 302 by a specific magnification factor achieved through lens 434, light source 428 is activated and the remaining light sources 406, 416 are deactivated. Light rays 444 pass through dichroic splitters 430, 420 and 418 and are reflected by dichroic splitter 404 based on the wavelength of the light rays. These light rays are then re-directed by mirror 402 to illuminate device 302. In turn, light rays 440, representing an image of device 302, emerges from lens 304, are reflected by mirror 402 as reflected light rays 442 and directed toward dichroic splitter 404. As mentioned above, the wavelength of the light rays 446 are such that they are reflected by splitter 404 and pass through splitters 418, 420. The bottom surface of splitter 430 has different properties that that of the top surface of splitter 430. As a result, light ray 446 are reflected by splitter 430 rather than passing through it. These reflected rays 448 pass through aperture 432 and are in turn magnified by lens 434. Light rays 450, representing the magnified image of a portion of device 302 are next redirected by mirror 436 as reflected light rays 452, which in turn, based on the wavelength of the light rays, pass through dichroic splitters 426 and 414, and are received by detector 316, such as a CCD or CMOS camera, or a position sensitive detector (PSD). As such, detector 316 received a magnified image of device 302 based on the wavelength of the light used to illuminate the device. Similarly, the path of light used to illuminate device 302 and its reflected image is based on the wavelength of light sources 406 and 416.

As can be appreciated by one of skill in the art, this approach may be modified and expanded to use more than three light sources and magnification paths as desired.

Although the invention has been described with reference to exemplary embodiments, it is not limited thereto. Rather, the appended claims should be construed to include other variants and embodiments of the invention which may be made by those skilled in the art without departing from the true spirit and scope of the present invention.

What is claimed is:

1. A vision system for use with a light source and providing a plurality of images of a device, the system comprising:
    a first beamsplitter for receiving an image of the device illuminated by the light source, the beamsplitter providing a plurality of images of the device;
    a plurality of optical elements for receiving respective ones of the plural images of the device, each of the plurality of optical elements magnifying the image by a predetermined magnification factor to produce a plurality of magnified images; and
    a second beamsplitter for receiving the plurality of magnified images and passing one of the magnified images based on a wavelength of the light source.

2. The vision system according to claim 1, further comprising an optical detector to receive the filtered magnified images from the second beamsplitter.

3. The vision system according to claim 2, wherein the optical detector is a camera.

4. The vision system according to claim 2, wherein the optical detector is a position sensitive detector.

5. The vision system according to claim 1, wherein the light has a wavelength in one of i) a visible spectrum and ii) an ultraviolet spectrum.

6. The vision system according to claim 1, wherein the first and second beamsplitter are each dichroic splitters.

7. The vision system according to claim 1, wherein the second beamsplitter filters undesired Illumination from each of the plurality of magnified images.

8. The vision system according to claim 1, wherein the plurality of optical elements are lenses.

9. The vision system according to claim 8, wherein each of the lenses has a predetermined magnification factor different from one another.

10. The vision system according to claim 1, further comprising:
    a first mirror coupled between the first beam splitter and the second optical element; and
    a second mirror coupled between the second optical element and the second beam splitter,
    wherein the first and second mirrors direct light form the first beamsplitter through the second optical element and onto the second beamsplitter.

11. A method for providing a plurality of magnified images of a device, the method comprising the steps of:
    illuminating the device with light having a first wavelength;
    receiving an image of the device illuminated by the light;
    splitting the image into a plurality of images based on the first wavelength of the light;
    magnifying the plurality of images;
    filtering out a portion of the plurality of magnified images based on the first wavelength of the light; and
    passing one filtered magnified image to an optical detector.

12. A method for providing a plurality of magnified images of a device, the method comprising the steps of:
    illuminating the device with a light;
    receiving an image of the device illuminated by the light;
    providing a plurality of images of the device based on the wavelength of the light;
    receiving respective ones of the plural images of the device;
    magnifying each of the respective ones of the plural images of the device by a predetermined magnification factor to produce a plurality of magnified images;
    receiving the plurality of magnified images;
    passing one of the plurality of magnified images and detecting the one magnified images.

13. A vision system for use with a plurality of light sources and providing a respective plurality of images of a device, the system comprising:
    a first beam splitter for receiving an image of the device illuminated by a first one of the plurality of light sources, the beam splitter providing a first image of the device;
    a second beam splitter for receiving an image of the device illuminated by a second one of the plurality of light sources, the beam splitter providing a second image of the device;
    a third beam splitter for receiving an image of the device illuminated by a third one of the plurality of light sources, the beam splitter providing a third image of the device;
    a plurality of optical elements for receiving a respective one of the first, second and third plural images of the device, each of the plurality of optical elements magnifying the image by a predetermined magnification factor to produce a respective magnified image; and
    a detector for receiving one of the magnified images based on which of the plurality of light sources illuminates the device.

14. The vision system according to claim 13, wherein each of the plurality of light sources has a wavelength different from that of the remaining plurality of light sources.

15. The vision system according to claim 14, wherein the plurality of light sources is at least three light sources.

* * * * *